United States Patent
Cho et al.

(10) Patent No.: US 6,254,885 B1
(45) Date of Patent: *Jul. 3, 2001

(54) ORAL CYCLOSPHORIN FORMULATIONS

(75) Inventors: Moo J. Cho, Chapel Hill, NC (US); Ralph E. Levy, Pleasanton; Philippe J. Pouletty, Atherton, both of CA (US)

(73) Assignees: SangStat Medical Corporation, Menlo Park, CA (US); The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/037,176

(22) Filed: Mar. 9, 1998

Related U.S. Application Data

(63) Continuation of application No. 08/620,021, filed on Mar. 21, 1996, now Pat. No. 5,766,629, which is a continuation-in-part of application No. 08/519,689, filed on Aug. 25, 1995, now Pat. No. 5,834,017.

(51) Int. Cl.$^7$ ................................ A61K 9/10; A61K 9/48

(52) U.S. Cl. ........................ 424/455; 514/885; 514/962; 514/975

(58) Field of Search ........................... 424/455; 514/885, 514/962, 975

(56) References Cited

U.S. PATENT DOCUMENTS

| 506,219 | 4/1893 | Desai . |
| 4,117,118 | 9/1978 | Harri et al. . |
| 4,220,641 | 9/1980 | Traber et al. . |
| 4,329,332 | 5/1982 | Couvreur et al. ........................ 424/9 |
| 4,388,307 | 6/1983 | Cavanak . |
| 4,489,055 | 12/1984 | Couvreur et al. ...................... 424/7.1 |
| 4,501,726 | 2/1985 | Schröder et al. ...................... 424/1.1 |
| 4,780,316 | 10/1988 | Brox . |
| 4,792,449 | 12/1988 | Ausman et al. . |

(List continued on next page.)

FOREIGN PATENT DOCUMENTS

| 2009533 | 9/1990 | (CA) . |
| 1326995 | 2/1994 | (CA) . |
| 2106827 | 3/1994 | (CA) . |
| 43 40 781 | 6/1995 | (DE) . |
| 195 39 860 | 5/1996 | (DE) . |
| 0 572 942 A2 | 12/1993 | (EP) . |
| 0 589 843 | 3/1994 | (EP) . |

(List continued on next page.)

OTHER PUBLICATIONS

Tarr & Yalkowsky, "Enhanced Intestinal Absorption of Cyclosporine in Rats Through the Reduction of Emulsion Droplet Size," Pharmaceutical Research (1989), 6:40–43.

Abdallah and Mayersohn, "The Preparation and Evaluation of a Tablet Dosage Form of Cyclosporine in Dogs," Pharmaceutical Research (1991), 8:518–522.

Sato et al., "Enhancement of The Intestinal Absorption of Cyclosporine Derivative by Milk Fat Globule Membrane," Biol. Pharm. Bull. 17:1526–1528.

(List continued on next page.)

*Primary Examiner*—Edward J. Webman
(74) *Attorney, Agent, or Firm*—Flehr Hohbach Test Albritton & Herbert LLP; Richard F. Trecartin

(57) ABSTRACT

Improved oral cyclosporin formulations which have high bioavailability and are capable of admiration in hard capsules are provided. In the subject formations, cyclosporin is delivered in an orally acceptable vehicle comprising at least one alkanol solvent of from 2 to 3 carbon atoms in combination with at least one non-ionic surfactant. The subject formalations may further comprise at least one cosolvent, where cosolvents of interest include fatty acids and diols. The subject formulations find use in immuno-suppressive therapy.

17 Claims, 3 Drawing Sheets

U.S. PATENT DOCUMENTS

| | | |
|---|---|---|
| 4,889,723 | 12/1989 | Kim et al. . |
| 4,945,121 | 7/1990 | Micale et al. ............... 523/339 |
| 4,970,076 | 11/1990 | Horrobin . |
| 4,990,337 | 2/1991 | Kurihara et al. . |
| 4,996,193 | 2/1991 | Hewitt et al. . |
| 5,047,396 | 9/1991 | Orban et al. . |
| 5,051,402 | 9/1991 | Kurihara et al. . |
| 5,118,493 | 6/1992 | Kelley et al. . |
| 5,118,528 | 6/1992 | Fessi et al. ............... 427/213.36 |
| 5,122,383 | 6/1992 | Heiber et al. . |
| 5,133,908 | 7/1992 | Stainmesse et al. ........... 264/4.1 |
| 5,154,930 | 10/1992 | Popescu et al. . |
| 5,302,401 | 4/1994 | Liversidge et al. ............ 424/501 |
| 5,326,552 | 7/1994 | Na et al. ............... 424/4 |
| 5,342,625 | 8/1994 | Hauer et al. . |
| 5,350,741 | 9/1994 | Takada . |
| 5,352,459 | 10/1994 | Hollister et al. ............ 424/489 |
| 5,364,632 | 11/1994 | Benita et al. . |
| 5,389,382 | 2/1995 | List et al. ............ 424/499 |
| 5,393,791 | 2/1995 | Roberts . |
| 5,407,609 | 4/1995 | Tice et al. ............ 264/46 |
| 5,429,824 | 7/1995 | June ............ 424/489 |
| 5,430,017 | 7/1995 | Antalne et al. . |
| 5,472,749 | 12/1995 | Dravid et al. ............ 427/580 |
| 5,504,068 | 4/1996 | Komiya et al. . |
| 5,518,738 | 5/1996 | Eickhoff et al. ............ 424/493 |
| 5,543,158 | 8/1996 | Gref et al. ............ 424/501 |
| 5,543,393 | 8/1996 | Kim et al. . |
| 5,565,188 | 10/1996 | Wong et al. ............ 424/9.411 |
| 5,573,783 | 11/1996 | Desieno et al. ............ 424/490 |
| 5,585,020 | 12/1996 | Becker et al. ............ 219/121.85 |
| 5,587,143 | 12/1996 | Wong et al. ............ 424/9.1 |
| 5,589,455 | 12/1996 | Woo . |
| 5,614,219 | 3/1997 | Wunderlich et al. ............ 424/472 |
| 5,614,491 | 3/1997 | Walch et al. . |
| 5,620,708 | 4/1997 | Amkraut et al. ............ 424/491 |
| 5,629,021 | 5/1997 | Wright ............ 424/489 |
| 5,641,515 | 6/1997 | Ramtoola et al. ............ 424/189 |
| 5,665,277 | 9/1997 | Johnson et al. ............ 264/6 |
| 5,665,331 | 9/1997 | Bagchi et al. ............ 424/9.45 |
| 5,674,531 | 10/1997 | Ahlers et al. ............ 424/489 |
| 5,683,723 | 11/1997 | Spenlehauer et al. ............ 424/501 |
| 5,702,727 | 12/1997 | Amkraut et al. ............ 424/491 |
| 5,705,194 | 1/1998 | Wong et al. ............ 424/489 |
| 5,705,196 | 1/1998 | Valdivia et al. ............ 424/497 |
| 5,716,642 | 2/1998 | Bagchi et al. ............ 424/489 |
| 5,717,030 | 2/1998 | Dunn et al. ............ 523/111 |
| 5,733,925 | 3/1998 | Kuntz et al. ............ 514/449 |
| 5,744,153 | 4/1998 | Yewey et al. ............ 424/426 |
| 5,766,635 | 6/1998 | Spenleuhauer et al. ............ 424/489 |
| 5,780,044 | 7/1998 | Yewey et al. ............ 424/426 |
| 5,811,447 | 9/1998 | Kuntz et al. ............ 514/411 |
| 5,833,647 | 11/1998 | Edwards ............ 604/22 |
| 5,843,509 | 12/1998 | Salve et al. ............ 424/489 |

FOREIGN PATENT DOCUMENTS

| | | |
|---|---|---|
| 0 650 721 A1 | 5/1995 | (EP) . |
| 0 712 631 | 5/1996 | (EP) . |
| 2 015 339 | 9/1979 | (GB) . |
| 2 200 048 | 7/1988 | (GB) . |
| 2 209 671 | 5/1989 | (GB) . |
| 2 211 848 | 7/1989 | (GB) . |
| 2 221 157 | 1/1990 | (GB) . |
| 2 224 205 | 5/1990 | (GB) . |
| 2 228 198 | 8/1990 | (GB) . |
| 2 230 440 | 10/1990 | (GB) . |
| 55-62021 | 5/1980 | (JP) . |
| 4-253907 | 9/1992 | (JP) . |
| 5-58906 | 3/1993 | (JP) . |
| WO 91/16057 | 10/1991 | (WO) . |
| WO 92/09299 | 6/1992 | (WO) . |
| WO 92/18105 | 10/1992 | (WO) . |
| WO 93/00106 | 1/1993 | (WO) . |
| 93/20833 | 10/1993 | (WO) . |
| WO 93/23010 | 11/1993 | (WO) . |
| WO 94/23733 | 10/1994 | (WO) . |
| WO 95/06464 | 3/1995 | (WO) . |
| 97/22358 | 6/1997 | (WO) . |
| 98/40094 | 9/1998 | (WO) . |

OTHER PUBLICATIONS

Benmoussa et al., "Cyclosporin Absorption Is Impaired by the Fat Substitutes, Sucrose Polyester and Tricarballylate Triester, in the Rat," Pharmaceutical Research (1994), 11:1458–1461.

Trull et al., "Cyclosporin Absorption From Microemulsion Formulation in Liver Transplant Recipient," The Lancet (1993), 341:433.

Ferrea et al., "Oral Microemulsion Formulation Substitutes for Intravenous Cyclosporin in Child with Graft–Versus–Host Disease," The Lancet (1994), 344:480–481.

Reymond et al., "In Vivo Model for Ciclosporin Intestinal Absorption in Lipid Vehicles," Pharmaceutical Research (1988), 5:677–679.

Ritschel et la., "Improvement of Peroral Absorption of Cyclosporine A By Microemulsions," Meth. Find Exp. Clin. Pharmacol. (1990), 12:127–134.

Reymond and Sucker, "In Vitro Model for Ciclosporin Intestinal Absorption in Lipid Vehicles," Pharmaceutical Research (1988), 5:673–676.

Cavanak and Sucker, "Formulation of Dosage Forms," Prog. Allergy (1986), 38:65–72.

ORAL CYCLOSPHORIN FORMULATIONS

CROSS-REFERENCE TO RELATED APPLICATIONS

This is a continuation of application Ser. No. 08/620,021 filed Mar. 21, 1996, now U.S. Pat. No. 5,766,629 which is a now U.S. Pat. No. 5,834,017, continuation-in-part of application Ser. No. 08/519,689 filed Aug. 25, 1995, which application is herein incorporated by reference.

INTRODUCTION

1. Field of the Invention

The field of this invention is oral cyclosporin formulations.

2. Background

Despite efforts to avoid graft rejection through host-donor tissue type matching, in the majority of transplantation procedures where a donor organ is introduced into a host, immunosuppressive therapy is critical to the maintained viability of the donor organ in the host. A variety of immunosuppressive agents have been employed in transplantation procedures, including azathioprine, methotrexate, cyclophosphamide, FK-506, rapamycin and corticosteroids. Agents finding increased use in immunosuppressive therapy due to their preferential effect on T-cell mediated reactions are the cyclosporins.

Cyclosporins are a class of cyclic polypeptides consisting of eleven amino acids which are produced as a metabolite by the fungus species Tolypocladium inflatum Gams. Cyclosporins have been observed to reversibly inhibit immunocompetent lymphocytes, particularly T-lymphocytes, in the $G_0$ or $G_1$ phase of the cell cycle. Cyclosporins have also been observed to reversibly inhibit lymphokine production and release. Although a number of cyclosporins are known, Cyclosporin A is the most widely used.

Use of Cyclosporin A has been reported to prolong the survival of allogeneic transplants involving skin, heart, kidney, pancreas, bone marrow, small intestine and lung. In allogeneic transplantations, Cyclosporin A has been shown to suppress humoral immunity and, to a greater extent, cell mediated immune reactions, including: allograft rejection, delayed hypersensitivity, experimental allergic encephalomyelitis, Freund's adjuvant arthritis, and graft vs. host disease. Although success has been realized with Cyclosporin A, following transplantation administration of the agent must be continued since the benefits of cyclosporin therapy are reversible and graft rejection occurs once administration of Cyclosporin A is discontinued.

Although cyclosporin formulations for both oral and intravenous administration have been developed, oral administration of cyclosporin is preferred because of the ease of administration and greater patient acceptance. Furthermore, intravenous administration of cyclosporin can result in anaphylactic reactions, a side effect not observed with oral formulations. Oral cyclosporin formulations which have been developed and are currently marketed include both soft gelatin capsule and solution formulations, both of which are sold under the trademarks SANDIMMUNE® and NEORALS™.

In using oral cyclosporin formulations in immunosuppressive therapy, both the care giver and manufacturer must be cognizant of many issues. With oral cyclosporin formulations, cydosporin bioavailablity can be limited because of cyclosporin's immiscibility in water and the tendency of cyclosporin to precipitate in aqueous environments. In addition, the concentration of cyclosporin present in oral formulations can be limited due to cyclosporin's hydrophobic nature. Furthermore, cyclosporin absorption by the gastrointestinal tract can be erratic from one formulation batch to the next, requiring constant monitoring of cyclosporin blood levels during treatment. Finally, packaging and storage stability are an issue with oral formulations. For example, with soft gelatin capsule formulations of cyclosporin, air tight packaging must be employed, which is inconvenient due to bulkiness and high cost. Furthermore, cyclosporine formulations may be unstable at lower temperatures, as cyclosporine crystalization may occur.

Thus, desirable oral cyclosporin formulations would be formulations that address at least some of the above issues. Ideally, oral formulations would promote high bioavailability, comprise high concentrations of cyclosporin and would be amenable to preparation in hard capsule form.

Relevant Literature

Physician's Desk Reference (1994) pp 2071–2074 describes oral cyclosporin formulations curly sold under the trademark SANDIMMUNE®.

Oral cyclosporine formulations are also described in the NEORAL™ package insert, (1995) (Sandoz Pharmaceuticals Corporation, East Hanover, N.J., 07936).

U.S. Patents of interest describing cyclosporins and derivatives thereof include: 4,220,641; 4,639,434; 4,289, 851; and 4,384,996. U.S. Pat. No. 5,047,396 describes an intravenous preparation for administration of cyclosporin. U.S. Pat. Nos. 4,388,307; 4,970,076 and 4,990,337 describe the preparation of oral cyclosporin formulations.

The preparation of hard capsules for the oral delivery of pharmaceutical formulations is described in U.S. Pat. Nos. 4,822,618; 4,576,284; 5,120,710; and 4,894,235.

BRIEF SUMMARY OF THE INVENTION

Oral cyclosporin formulations, and methods for their use in immunosuppressive therapy, are provided. In the subject formulations, cyclosporin is present in an orally acceptable vehicle comprising at least one alkanol solvent of from 2 to 3 carbon atoms in combination with at least one non-ionic surfactant. The subject formulations may further comprise one or more cosolvents, where cosolvents of interest are fatty acid esters and diols. The cyclosporin formulations can be packaged as hard capsules.

DESCRIPTION OF THE SPECIFIC EMBODIMENTS

Figure 1:
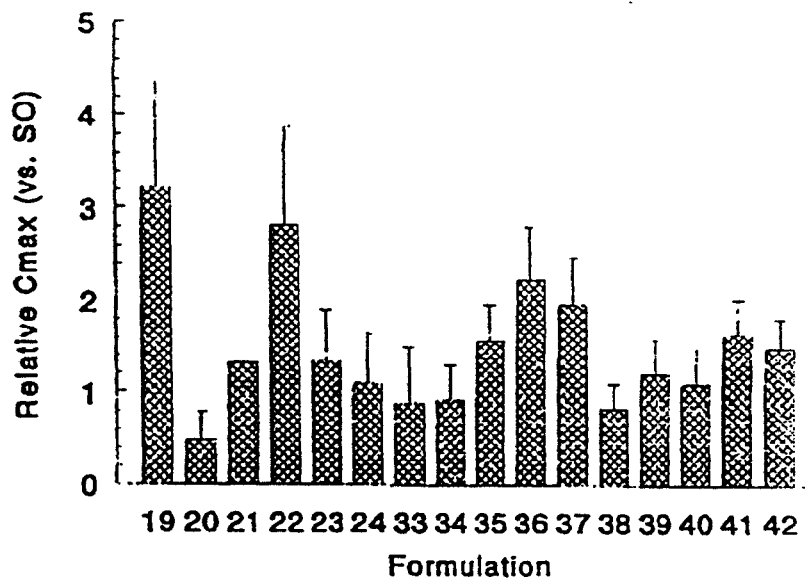
FIG. 1 provides the cyclosporin peak concentration ($C_{max}$) achieved in rats for several oral formulations according to the subject invention, where the $C_{max}$ is shown as a relative value compared to the $C_{max}$ achieved with SANDIMMUNE® ORAL formulation (SO).

Oral cyclosporin formulations are provided which promote bioavailability and can be formulated as capsules, particularly hard capsules. In the subject formulations, cyclosporin is present in an orally acceptable vehicle comprising at least one alkanol solvent of from 2 to 3 carbon atoms in combination with at least one non-ionic surfactant. The subject formulations may father comprise at least one cosolvent, where cosolvents of interest include fatty acid esters and diols. Each of the components of the subject formulations are pharmaceutically acceptable. In addition to providing for high bioavailability, the subject formulations provide for reproducible cyclosporin absorption from one batch of a particular formulation to the next. The subject formulations find use in immunosuppressive therapy.

A number of cyclosporins are known in the art to exhibit immunosuppressive activity and may be delivered in the subject oral formulations. Cyclosporins that may be administered in the subject formulations include Cyclosporin A, Cyclosporin B, Cyclosporin C, Cyclosporin D and Cyclosporin G, as well as synthetic analogs thereof See Merck Index (1989) 2759. The subject oral formulations are particularly suited for the delivery of Cyclosporin A. When delivered in the subject formulations, Cyclosporin A will be present in concentrations ranging from 50 to 150 mg/ml, usually 100 to 150 mg/ml, based on the volume of the vehicle component of the formulation.

The vehicle component of the subject formulations will include an alkanol solvent component, where the alkanol solvent component will comprise at least one alkanol and usual no more than three different alkanols, more usually no more than two different alkanols, where the alkanols will usual be from 2 to 3 carbon atoms, and from 1 to 2 hydroxy groups, such that there is no more than 1 hydroxy group per 1.5 carbon atoms. Suitable alkanols include ethanol and propylene glycol. The total amount of alkanol solvent in the formulation will be at least about 1% (v/v), usually at least about 3% (v/v) and may be as high as 95% (v/v), but will generally range from about 5 to 75% (v/v), by from about 5 to 60% (v/v), and more usually from about 10 to 60% (v/v) of the formulation. When ethanol is present in the formulation as an alkanol solvent, the amount of ethanol may range from 5 to 20% (v/v), usually from about 5 to 15% (v/v) of the formulation, while when propylene glycol is present as an alkanol solvent, the amount of propylene glycol in the subject formulation may range from about 5 to 90% (v/v), usually from about 5 to 85% (v/v), more usually from about 10 to 50% (v/v) of the formulation.

Also present in the orally acceptable vehicle will be at least one non-ionic polyoxyalkylene surfactant, usually not more than two polyoxyalkylene non-ionic surfactants. The polyoxyalkylene surfactants will have a hydrophilic-lipophilic-balance (HLB) of from about 5 to 20, usually from about 8 to 16. Preferably, the polyoxyalkylene non-ionic surfactants employed in the subject formulations will be polyoxyethylene compounds. Polyoxyethylene compounds of interest include: ethoxylated alcohols, i.e. polyoxyethylene alcohols or ethoxylated fatty alcohols, where the alcohol moieties are generally of from 10 to 18, usually from 10 to 14 carbon atoms, as well as ether and ester substituents thereof and polyoxyethylene derivatives of fatty acid partial esters, usually monoesters, of polyols of from 4 to 6 carbon atoms, usually 6 carbon atoms, where the polyols may be polyol anhydrides e.g. sorbitan. The fatty acid moieties of the subject surfactant will typically range from 10 to 18 carbon atoms. The number of ethylenoxide groups will generally be in the range of 2 to 30, usually in the range from about 2 to 25. Preferred surfactants are polyoxyethylene (4) lauryl ether (BRIJ 30®) and polyoxyethylene (20) mono sorbitan mono-oleate (TWEEN 80®. The total amount of non-ionic surfactants present in the subject formulations will range from 5 to 65%, usually from about 5 to 60% (v/v) of the formulation. Where TWEEN 80® is present in the formulation, it will usually be present in amounts ranging from 5 to 60%, more usually from about 10 to 50% (v/v) of the formulation. When BRIJ 30® is present in the subject formulation, it will usually be present in amounts ranging from 10 to 45%, more usual from about 15 to 40% (v/v) of the formulation.

The subject formulations may further comprise one or more cosolvents, usually not more than three different cosolvents, more usually not more than two different cosolvents, where suitable cosolvents include fatty acid esters and diols, where the cosolvent may be 100% fatty acid ester, 100% diol, or combination thereof. The total amount of cosolvent present in the formulation may range from about 20 to 80% (v/v) and will usually range from about 25 to 75% (v/v). When present in the formulation, the ratio of cosolvent to solvent in the subject formulations may range from about 1:1 to 15:1, but will usually range from about 1:1 to 13:1.

Fatty acid esters which may serve as cosolvents in the subject formulations are those fatty acid esters where the hydrocarbon chain of the fatty acid is from 12 to 18, usually 14 to 18 carbon atoms in length, where the fatty acid ester will be a mono-ester of a lower alkanol. Suitable fatty acid esters will generally comprise an even numbered fatty acid chain, where the hydrocarbon chain may be saturated or unsaturated, usually having not more than two sites of unsaturation. Fatty acids of interest will generally be of plant or mammalian origin and include palmitate, stearate, palmitoleate, linoleate, linolenate and the like, particularly myristate and oleate. The alcohol of the fatty acid mono-ester will be a lower alkanol of from 2 to 4 carbon atoms in length, usually 2 to 3 carbon atoms in length, with or without branches. Fatty acid esters of particular interest are isopropyl myristate and ethyl oleate. Isopropyl myristate, when present, will range from about 55 to 75% (v/v), and ethyl oleate, when present, will range from about 35 to 75% (v/v) ofthe total formulation. Usually the fatty acid ester will be present in an amount at least about equal (v/v) and up to 8 times the amount of surfactant in the formulation, usually not greater than 5 times the amount of surfactant in the formulation (v/v).

Diols may also be present in the subject formulations, where the diols may be present in addition to, or in lieu of, the fatty acid ester cosolvent. Diols of interest as cosolvents are generally liquids at physiologic temperatures and include diols of from 8 to 28 carbon atoms, usually 16 to 20 carbon atoms, where the diol may be a polyoxyalkylene diol, where alkylene is of from 2 to 3 carbon atoms. Suitable diols for use as cosolvents may range from about 200 to 800 daltons, usually from about 200 to 650 daltons. Diols of particular interest include polyethylene glycols, particularly polyethylene glycol 200 ($PEG_{200}$), polyethylene glycol 400 ($PEG_{400}$), polyethylene glycol 600 ($PEG_{600}$), and the like, with PEG$_{400}$ being preferred. When present as cosolvents in the subject formulations, the diols will range from about 5 to 60% (v/v), usually from 5 to 55% (v/v) of the formulation.

In the subject formulations, the cosolvents themselves may impart desirable physical properties to the formulation, such as viscosity, stability and the like. Where desired, the formulation may further comprise additional agents which impart desired physical properties to the formulation, such as thickening agents, suspending agents, solidifying agents, and the like, where such agents include acacia, carboxymethylcellulose, hydroxypropylcellulose, lecithin, methyl cellulose, high molecular weight polyethylene glycols, e.g those polyethylene glycols with molecular weights ranging from about 1000 to 6000, usually 1000 to 5000 daltons, povidone, sodium alginate, tragacanth, and the like. Also present in the subject formulations may be a number of minor components which provide various functions, such as enzyme inhibitors, preservatives, antioxidants, antimicrobial agents, stabilizers and the like. The total amount of these thickening agents and other additives, when present in the formulation, will normally not be greater than 5 weight %, usually 2 weight %, more usually 1 weight % of the formulation. A number of excipients may also be present in the subject formulations, as is known in the art.

The subject formulations are stable over a wide range of temperatures, where by stable is meant that the physical integrity of the formulation is not comprised, e.g. crystallization of the cyclosporin active agent does not occur. Included within the temperature range over which the subject formulations are stable are lower temperatures, such as those employed in refrigerated storage, where such lower temperatures typically range from about 0 to 15° C., more typically from about 2 to 8° C.

The subject formulations are suitable for administration in capsule form, e.g. hard and soft capsules. Methods of producing hard capsules comprising liquid formulations are known in the art and described in U.S. Pat. Nos. 4,822,618 and 4,576,284, the disclosures of which are herein incorporated by reference. Generally, hard capsules that find use with the subject formulations will comprise two parts: a shell component and a cap component. The shell and cap components fit together to produce an enclosed cavity of defined volume sealed in a hard capsule shell. The shell and cap components may be fabricated from a hydrophilic polymer, such as starch or gelatin. In preparing the hard capsules, the liquid formulation will be poured into the shell component and then the capsule will be sealed by fitting the cap component over the shell component. The seal between the two components may be secured, thereby preventing leakage of the enclosed formulation from the capsule, by using a sealant as described in EP 116744, the disclosure of which is herein incorporated by reference. To avoid degradation in the stomach, capsules comprising the subject formulations may be coated with an enteric coating which inhibits degradation of the capsule in the acidic environment of the stomach. A variety of enteric coatings are known in the art. See for example, U.S. Pat. No. 5,206,219, the disclosure of which is herein incorporated by reference.

The subject formulations find use in immunosuppressive therapy. Immunosuppressive therapy is indicated in a wide variety of diseases, including idiopathic nephrotic syndrome, type I insulin-dependent diabetes, Behcet's syndrome, active Crohn's disease, a plastic anemia, severe corticosteroid-dependent asthma, psoriasis, rheumatoid arthritis, and other diseases where the immune system may play a pathogenic role. Of particular interest is the use of the subject formulations in transplant situations, including both allogeneic and xenogeneic organ, tissue or cell transplantation, where immunosuppression is desired to ensure maintained viability of the transplanted organ or tissue or cell following transplantation, i.e. to prevent graft rejection or prevent graft vs. host disease, e.g. following bone marrow transplantation.

In using the subject formulations to provide immunosuppressive therapy to a host, an effective amount of cyclosporin will be orally administered to achieve the desired level of immunosuppression in the host, depending on the particular condition to be treated. With transplantation, usually an initial dosage of cyclosporin will be administered prior to operation. Following transplantation of the donor organ to the host, the cyclosporin will be administered repeatedly, i.e. chronically, to the host to maintain immunosuppression. The initial dosage will be administered 4 to 12 hours prior to transplantation and may range from 10 to 18 mg/kg host, usually 10 to 15 mg/kg host. Following the operation, the initial dosage will usually be continued on a daily basis for a period of 1 to 3 weeks, usually 1 to 2 weeks. The dosage may then be tapered to a maintenance dosage of 3 to 10 mg/kg per day, usually 3 to 6 mg/kg per day. The rate at which the dosage is tapered to the maintenance level may range from 3 to 8% per week and will usually be about 5% per week. The dosage will typically be adjusted based on trough blood levels to maintain a concentration of 150 to 250 ng/ml, as measured by HPLC, RIA, ELISA or TDx assay. The subject formulations may be administered in conjunction with additional agents, where adjunct therapy is recommended and is known in the art. For example, the subject formulations may be administered in conjunction with adrenal corticosteroids, azathioprine and the like.

Administration of the subject formulations in conjunction with transplantation of a donor organ to a host will result in a prolongation of the viability of the donor organ in the host as a result of suppression of the host's immune response to the presence of the donor organ. By "prolongation of viability" is meant that the donor organ remains viable in the host for a longer period of time than it would have had immunosuppressive therapy not been employed in conjunction with the transplantation. Thus, prolongation of viability includes maintenance of viability for an indefinite period of time. A donor organ is considered viable as long as it maintains functionality in the host environment.

The following examples are offered by way of illustration and not by way of limitation.

EXPERIMENTAL

Several oral cyclosporin formulations according to the subject invention were prepared. The bioavailability of cyclosporin in the prepared formulations was then observed in rats and humans.

I. Oral Cyclosporin Formulations

The following oral Cyclosporin A formulations were prepared. In each case, 100 mg CsA, the indicated amount of surfactant, and the indicated amount of ethanol or propylene glycol were added to a 1.0 ml volumetric flash, and the final volume of 1.0 ml was achieved by addition of a suitable volume of fatty acid ester and/or diol.

| Formulation | Composition | | |
|---|---|---|---|
| 19 | EtOH | 0.1 ml | (10%) |
| | Tween 80 | 300 mg | (0.278 ml) |
| | IM | q.s. to 1.0 ml | ((0.622 ml)(531 mg) |
| 20 | EtOH | 0.05 ml | (5%) |
| | Brij 30 | 350 mg | (0.368 ml) |
| | IM | q.s. to 1.0 ml | ((0.582 ml)(496 mg) |
| | PG | 0.05 ml | (5%) |
| | Brij 30 | 350 mg | (0.368 ml) |
| | IM | q.s. to 1.0 ml | ((0.582 ml)(496 mg) |
| 22 | EtOH | 0.1 ml | (10%) |
| | Tween 80 | 300 mg | (0.278 ml) |
| | EO | q.s. to 1.0 ml | ((0.622 ml)(541 mg) |
| 23 | EtOH | 0.05 ml | (5%) |
| | Brij 30 | 350 mg | (0.368 ml) |
| | EO | q.s. to 1.0 ml | ((0.582 ml) (506 mg) |
| 24 | PG | 0.05 ml | (5%) |
| | Brij 30 | 350 mg | (0.368 ml) |
| | EO | q.s. to 1.0 ml | ((0.582 ml) (506 mg) |
| 33 | EtOH | 0.1 ml | (10%) |
| | Brij 30 | 150 mg | (0.158 ml) |
| | IM | q.s. to 1.0 ml | ((0.742 ml)(633 mg) |
| 34 | EtOH | 0.1 ml | (10%) |
| | Brij 30 | 150 mg | (0.158 ml) |
| | EO | q.s. to 1.0 ml | ((0.742 ml)(646 mg) |
| 35 | EtOH | 0.1 ml | (10%) |
| | Tween 80 | 500 mg | (0.463 ml) |
| | PG | q.s. to 1.0 ml | ((0.437 ml)(453 mg) |
| 36 | EtOH | 0.1 ml | (10%) |
| | Tween 80 | 300 mg | (0.278 ml) |
| | PG | 100 mg | (0.097 ml) |
| | EO | q.s. to 1.0 ml | ((0.525 ml)(465 mg) |
| 37 | EtoH | 0.1 ml | (10%) |
| | Tween 80 | 300 mg | (0.278 ml) |
| | PEG 400 | 100 mg | (0.088 ml) |
| | EO | q.s. to 1.0 ml | ((0.534 ml)(464 mg) |
| 38 | EtOH | 0.1 ml | (10%) |
| | Brij 30 | 300 mg | (0.316 ml) |
| | PG | 100 mg | (0.097 ml) |
| | EO | q.s. to 1.0 ml | ((0.487 ml)(424 mg) |
| 39 | EtOH | 0.1 ml | (10%) |
| | Brij 30 | 300 mg | (0.316 ml) |
| | PG | 200 mg | (0.193 ml) |
| | EO | q.s. to 1.0 ml | ((0.391 ml)(340 mg) |
| 40 | PG | 300 mg | (290 ml) |
| | Brij 30 | 300 mg | (0.316 ml) |
| | EO | q.s. to 1.0 ml | ((0.394 ml)(343 mg) |
| 41 | EtOH | 0.05 ml | (5%) |
| | Brij 30 | 150 mg | (0.158 ml) |
| | Tween 80 | 100 mg | (0.093 ml) |
| | EO | q.s. to 1.0 ml | ((0.649 ml) (565 mg) |
| 42 | PG | 0.05 ml | (5%) |
| | Brij 30 | 150 mg | (0.158 ml) |
| | Tween 80 | 100 mg | (0.093 ml) |
| | EO | q.s. to 1.0 ml | ((0.649 ml) (565 mg) |
| 43 | EtOH | 0.10 ml | (10%) |
| | Tween 80 | 400 mg | (0.371 ml) |
| | PG | q.s. to 1.0 ml | (0.529 ml) |
| 44 | EtOH | 0.10 ml | (10%) |
| | Tween 80 | 400 mg | (0.371 ml) |
| | PEG$_{400}$ | q.s. to 100 ml | ((0.529 ml)(601 mg) |
| 45 | EtOH | 0.10 ml | |
| | Tween 80 | 300 mg | (0.278 ml) |
| | PG | approx.250 mg | (0.243 ml) |
| | PEG$_{400}$ | approx.250 mg | (0.220 ml) |
| 46 | EtOH | 0.10 ml | (10%) |
| | Tween 80 | 100 mg | (0.093 ml) |
| | PG | q.s. to 1.0 ml | (0.807 ml) |
| 48 | EtOH | 0.10 ml | |
| | Tween 80 | 200 mg | (0.186 ml) |
| | PG | approx.250 mg | (0.243 ml) |
| | PEG$_{400}$ | approx.250 mg | (0.220 ml) |
| 49 | EtOH | 0.10 ml | (10%) |
| | Tween 80 | 600 mg | (0.558 ml) |
| | PG | q.s. to 1 ml | (0.342 ml) |
| 50 | EtOH | 0.10 ml | (10%) |
| | Tween 80 | 300 mg | (0.278 ml) |
| | PG | q.s. to 1.0 ml | (0.622 ml) |

-continued

| Formulation | Composition | | |
|---|---|---|---|
| 51 | EtOH | 0.10 ml | (10%) |
| | Tween 80 | 200 mg | (0.186 ml) |
| | PG | q.s. to 1.0 ml | (0.714 ml) |
| 52 | EtOH | 0.05 ml | (5%) |
| | Tween 80 | 400 mg | (0.371 ml) |
| | PG | q.s. to 1.0 ml | (0.579 ml) |

PG = Propylene Glycol; EtOH ethanol
Brij 30 = polyoxyethylene (4) lauryl ether
Tween 80 = polyoxyethylene (20) mono sorbitan mono-oleate
IM = isopropyl myristate
EO = ethyl oleate II. In vivo Bioavailability Studies for Formulations 19–24 and 33–42

The bioavailability of cyclosporin in formulations 19–24 and 33–42 was studied as follows. As a measure of bioavailability, the following pharmacokinetic parameters were determined: (a) the peak blood concentration of cyclosporin ($C_{max}$); (b) time required to attain $C_{max}$ ($T_{max}$); and the area under the blood concentration time-curve time (AUC). In addition to formulations 19–24 and 33–42, the bioavailability of cyclosporin in SANDIMMUNE® Oral Solution (SO) under analogous conditions was observed for comparison purposes. For each of the above formulations, CsA-naive Sprague Dawley rats weighing 250–350 gm were fed pelletized standard food (Agway® 3000, Granville Mill, Greensboro, N.C.) and water ad libitum. One day prior to the experiment, silicone rubber cannulae were inserted into the right jugular and right femoral veins under light ether anesthesia. After overnight fast, CsA was administered by gavage.

Following administration, 200 µl blood samples were collected from the jugular vein in 0.5 ml polypropylene microfuge tubes containing 0.3 mg of lyophilized Na EDTA and vortexed immediately for 10 sec. The sampling times for animals subjected to oral formalations were 0, 0.5, 1, 2, 4, 8, 12, 24, 36, 48 and 72 hr after administration.

CsA, including some of its metabolites, was determined in whole blood by fluorescent polarization immunoassay (FPI) (TDx, Abbot Lab.). Briefly, 150 µl of the whole blood sample were quantitatively transferred to a 1.5 ml microfuge tube. Cells were lysed and dissolved with 50 µl of a surfactant-containing solubilizing reagent. Proteins were then precipitated out with 300 µl of acetonitrile. After centrifugation, the supernatant was subjected to the FPI assay in a TDx Autoanalyzer following the procedure recommended by Abbott Diagnostics. Since the TDx assay was originally developed for human blood, some of the recommended procedures were modified as follows. A series of standard solutions of known CsA concentration were prepared by adding a known amount of CSA to rat blood treated with EDTA When the CsA concentration in a sample was expected to be greater than 1.0 µg/ml, the blood sample was diluted 10-fold in a 0.1 M-phosphate buffer at pH 7.0. For diluted samples, another calibration curve was made using a series of standard solutions containing known amounts of CsA, which is volume-wise 10% in rat blood and 90% phosphate buffer.

Descriptive pharmacokinetic parameters were obtained from noncompartmental analyses. The peak concentration ($C_{max}$) and the time at which the peak concentration occurred ($T_{max}$) were estimated by inspection of the raw concentration-time profile for each rat. The area under the blood concentration-time curve (AUC) from time 0 through the last data point ($AUC_{0 \to t}$) was calculated according to the linear trapezoidal procedure. The residual area under the tail of the blood concentration-time curve ($AUC_{t \to \infty}$) was estimated as the ratio of the final observed concentration (C*) to the first-order rate constant associated with the terminal elimination phase of the concentration-time profile ($\lambda_z$). The rate contact $\lambda_z$ was determined by log-linear regression of the concentration-time data in the apparent terminal log-linear phase of the concentration-time profile (i.e., the final 3 to 5 data points, depending on the profile under analysis). The total AUC ($AUC_{t \to \infty}$) was taken as the sum of $AUC_{0 \to t}$ and $AUC_{t \to \infty}$.

Figure 2:
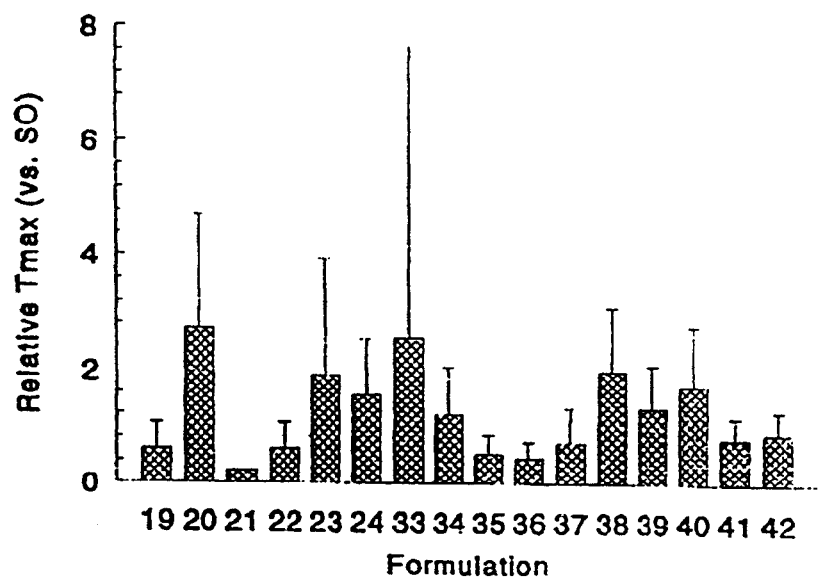
FIG. 2 provides the time at which $C_{max}$ occurred ($T_{max}$) for each of formulations shown in FIG. 1, where $T_{max}$ is provided as relative value compared to the $T_{max}$ of SANDIMMUNE® ORAL formation (SO).
Figure 3:
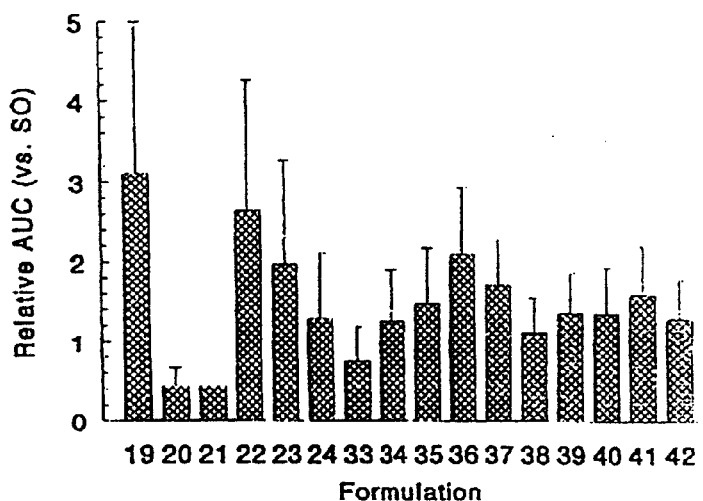
FIG. 3 provides the relative area under the blood concentration-time curve (AUC) for each of the formulations shown in FIG. 1, where AUC is provided as a relative value compared to the AUC value for SANDIMMUNE® ORAL formulation (SO).

The results for each formation were compared with the results obtained for SO, and are provided in FIGS. 1–3. The results demonstrate that, for the majority of the formulations, greater bioavailablity of cyclosporin is achieved with the subject formulations as compared with SANDIMMUNE® Oral Solution (SO), as indicated by the higher AUC values of the subject formulations.

III. In vivo Human Bioavilability of Formations 35, 43–46 and 48–52.

48 healthy males between the ages of 19 and 55 with no more than 20% deviation from ideal weight were used as test subjects. A single dose, fasted, randomized, double-blinded, three-way crossover study was conducted. The 48 subjects were randomized into 6 groups of 8 subjects. Each group received a single 300 mg dose of cyclosporin from the above formulations, or SANDIMMUNE® Oral Solution (SO), on three different occasions, where each occasion was separated by a 7-day washout period.

Subjects were required to fast 10 hours prior to, and 4 hours after, dosing. Water was allowed ad lib during the study, except for a 1 hour period prior through 2 hours following dosing. Prior to dosing, a 15 ml blood sample was drawn. For administrations, 3 ml aliquots of formulation (300 mg) was combined with 200 ml chocolate milk and orally ingested. 10 ml blood samples were drawn at t=0, 0.5, 1, 1.5, 2, 3, 4, 6, 8, 10, 12, 16, 20 and 24 hours. A post study 15 ml blood sample was also drawn.

Concentrations of cyclosporin A in the whole blood samples were assayed using the TDx (Abbott Diagnostics, N. Chicago, Ill.) according to the manufacturer's instructions.

Non-compartmental pharmacokinetics were derived using standard methods. The maximum whole blood concentration ($C_{max}$) and the time of its occurrence ($T_{max}$) were compiled from the concentration-time data. The area under the blood concentration time curve (AUC) was calculated by the linear trapezoidal rule to the last blood concentration above the limit of sensitivity (25 ng/nl) and extrapolated to infinity.

Figure 4:
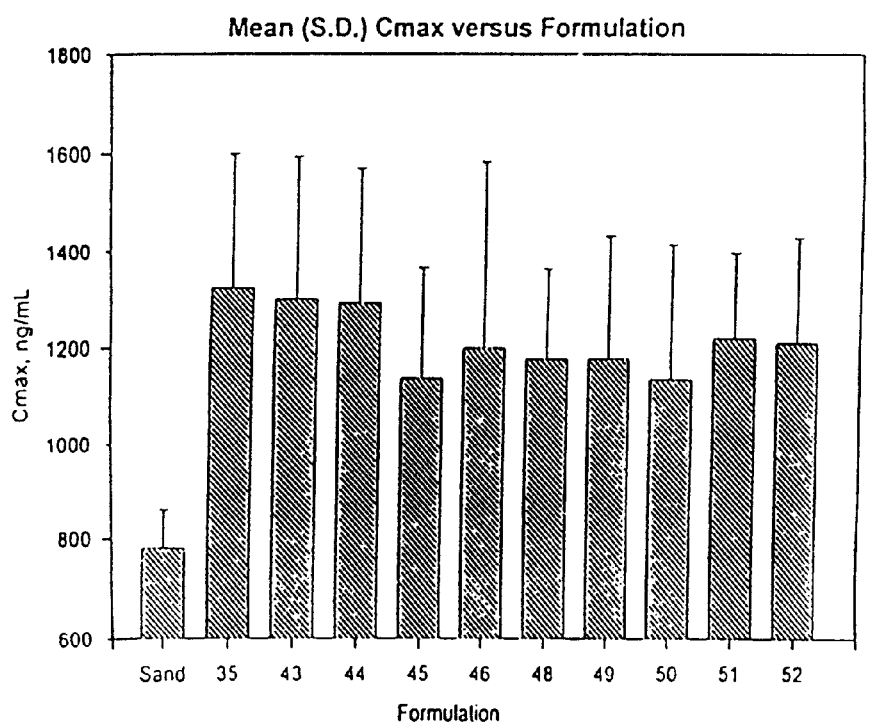
FIG. 4 provides the cyclosporin peak concentration ($C_{max}$) achieved in humans for several oral formulations according to the subject invention, as well as SANDIMMUNE® ORAL solution ("Sand" in the figure).
Figure 5:
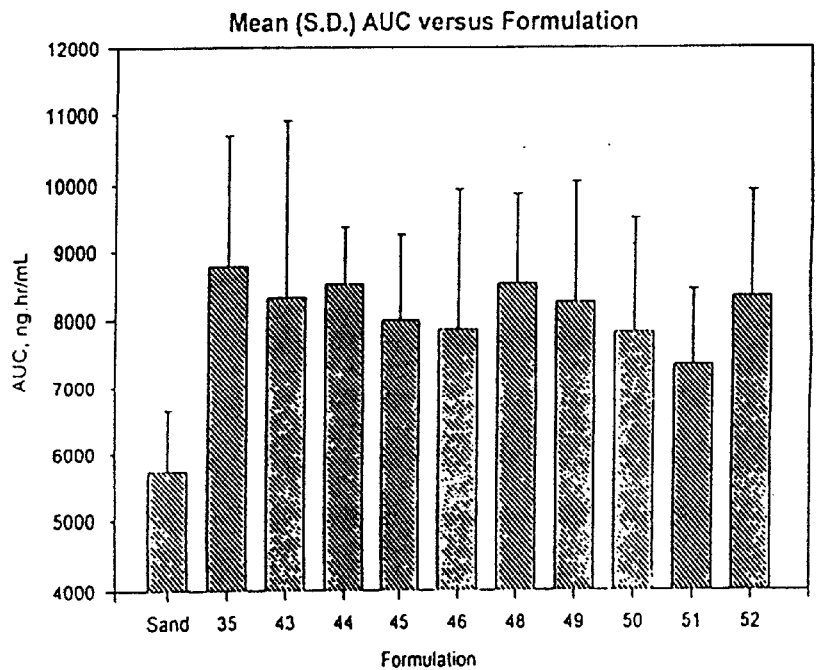
FIG. 5 provides the time at which $C_{max}$ occurred ($T_{max}$) for each of formulations shown in FIG. 4.
Figure 6:
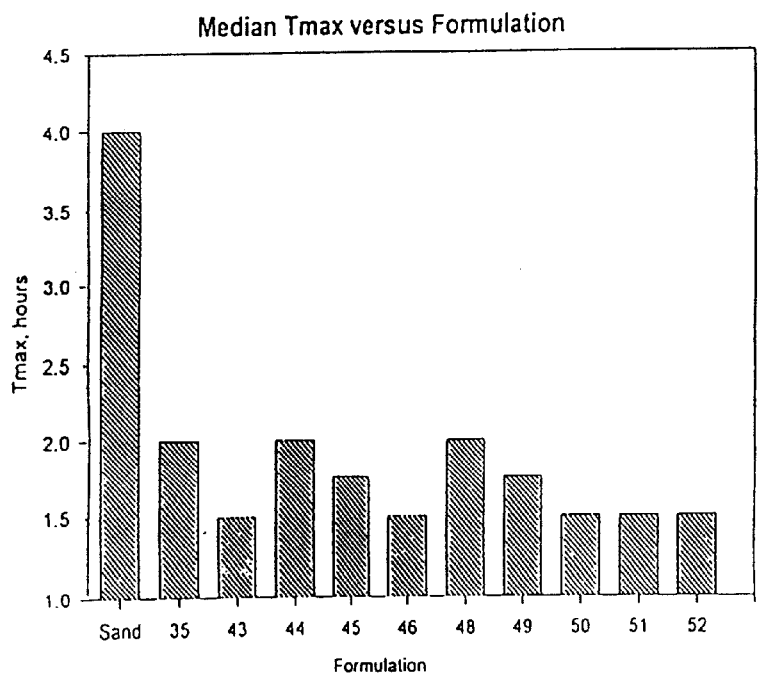
FIG. 6 provides the area under the blood concentration-time curve (AUC) for each of the formulations shown in FIG. 4.

The observed $C_{max}$, $T_{max}$ and AUC values for each formulation were averaged. The average values for each formulation are provided in FIGS. 4–6. The results demonstrate that for each formulation tested, Cmax occurred at least twice as fast as with SANDIMMUNE® Oral Solution (SO) under the same conditions. Furthermore, the AUC observed for the test formulations was at least 2000 ng·hr/ml greater than that observed for SANDIMMUNE® Oral Solution (SO) under the same conditions. Based on these results, formulations 35, 43–46 and 48–52 provide for greater bioavailability than SANDIMMUE® Oral Solution (SO).

From the above results and discussion, it is evident that novel cyclosporin formulations having high bioavailability are provided. The subject formulations are capable of comprising high concentrations of cyclosporin and are storage stable over a wide range of temperatures, including low temperatures commonly used in refrigeration. The subject formulations are amenable to delivery in capsule form, including hard capsule form, proving for ease of storage and handling.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cyclosporin formulation consisting essentially of:
    cyclosporin;
    at least one alkanol solvent of from 2 to 3 carbon atoms;
    at least one non-ionic polyoxyalkylene surfactant, wherein said surfactant is selected from the group consisting of polyoxyethylene alcohols and fatty acid monoesters of ethoxylated polyols of from 4 to 6 carbon atoms; and
    at least one cosolvent, wherein said cosolvent is selected from the group consisting of mono-esters of a lower alkanol and a fatty acid of from 14 to 18 carbon atoms and diols of from 8 to 28 carbon atoms.

2. The formulation according to claim 1, wherein said alkanol solvent is from about 5 to 75% (v/v) of said formulation.

3. The formulation according to claim 1, wherein said at least one non-ionic polyoxyalkylene surfactant is from about 5 to 65% (v/v) of said formulation.

4. The formulation according to claim 2, wherein said at least one cosolvent is from about 20 to 80% (v/v) of said formulation.

5. A cyclosporin formulation consisting essentially of:
    Cyclosporin A;
    at least one alkanol solvent selected from the group consisting of ethanol and propylene glycol, wherein said alkanol solvent is from about 5 to 75% (v/v) of said formulation;
    at least one non-ionic polyoxyethylene surfactant, wherein said non-ionic polyoxyethylene surfactant is selected from the group consisting of polyoxyethylene alcohols and mono-esters of ethoxylated sorbitans, and is from about 5 to 65% (v/v) of said formulation; and
    at least one cosolvent, wherein said at least one cosolvent is selected from the group consisting of a mono-ester of a lower alkanol of from 2 to 4 carbon atoms and a fatty acid of from 14 to 18 carbon atoms, wherein said cosolvent is from about 20 to 80% (v/v) of said formulation.

6. The formulation according to claim 5, wherein said non-ionic surfactant is selected from the group consisting of polyoxyethylene (4) lauryl ether and polyoxyethylene (20) mono sorbitan mono-oleate.

7. The formulation according to claim 5, wherein said formulation comprises two cosolvents, wherein one said cosolvents is a diol of from 8 to 28 carbon atoms.

8. The formulation according to claim 7, wherein said diol is a polyoxyethylene glycol.

9. A hard capsule cyclosporin formulation consisting essentially of:
    a hard capsule containing the oral formulation according to claims 1 or 5.

10. A method for achieving immunosuppression in a host, said method comprising:

administering to said host a cyclosporin formulation according to claims 1 or 5;

whereby immunosuppression in said host is achieved.

11. The method according to claim 10, wherein said at least one alkanol solvent is selected from the group consisting of ethanol and propylene glycol and is from about 5 to 75% (v/v) of said formulation.

12. The method according to claim 10, Wherein said at least one non-ionic polyoxyethylene surfactant is selected from the group consisting of polyoxyethylene (4) lauryl ether and polyoxyethylene (20) mono sorbitan mono-oleate.

13. The method according to claim 10, wherein at least one of said at least one cosolvents is a said fatty acid ester selected from the group consisting of isopropyl myristate and ethyl oleate.

14. A method according to claim 10, wherein at least one of said at least one cosolvents is polyethylene glycol 400.

15. A method for prolonging the viability of a donor organ in a host, said method comprising;

orally administering to said host in conjunction with transplantation of said donor organ a cyclosporin formulation according to claim 1.

16. The method according to claim 15, wherein said formulation is administered in a hard capsule.

17. The method according to claim 15, wherein said formulation is administered chronically after said transplantation.

\* \* \* \* \*